United States Patent [19]

Hock

[11] Patent Number: 5,295,902
[45] Date of Patent: Mar. 22, 1994

[54] BIOLOGICAL SAFETY CABINET
[75] Inventor: Kuah T. Hock, Champaign, Ill.
[73] Assignee: Forma Scientific, Inc., Marietta, Ohio
[21] Appl. No.: 880,185
[22] Filed: May 7, 1992
[51] Int. Cl.⁵ .............................................. B08B 15/02
[52] U.S. Cl. ........................................... 454/57; 454/66
[58] Field of Search ......................... 454/49, 56, 57, 66

[56] References Cited
U.S. PATENT DOCUMENTS

| 3,895,570 | 7/1975 | Eagleson, Jr. | 454/57 |
| 5,113,749 | 5/1992 | Perbix | 454/57 X |
| 5,195,922 | 3/1993 | Genco | 454/57 |

OTHER PUBLICATIONS

The Baker Company, Inc., SterilGARD, Vertical Laminar Flow Biological Safety Cabinet, pp. 30-36.

Primary Examiner—Harold Joyce
Attorney, Agent, or Firm—Wood, Herron & Evans

[57] ABSTRACT

A biological safety cabinet comprising an enclosure having two side walls, a rear wall, a bottom wall defining a work surface, a top wall and a front window, below which access can be had to the work surface, the enclosure defining a work area. A plenum surrounds the enclosure and communicates with the work area. A blower induces a negative pressure within the plenum to circulate contaminated air through a filter within the enclosure, which creates a downwardly directed air curtain of work area air below the window. A vertically oriented outwardly facing channel section is secured to each side wall adjacent the window. Each channel section has a downwardly and forwardly sloping upper end, a rear edge of which extends above a lower edge of the window and a front edge of which extends below the lower edge of the window. The plenum communicates with each channel. Ambient air and air within the air curtain adjacent upper lateral edges of the air curtain are accelerated downwardly by the channels to reduce the tendency of the ambient air and the cabinet side walls to decrease the velocity of the air curtain, thereby strengthening the air curtain and reducing a tendency of the ambient air and the work area air to interchange.

24 Claims, 3 Drawing Sheets

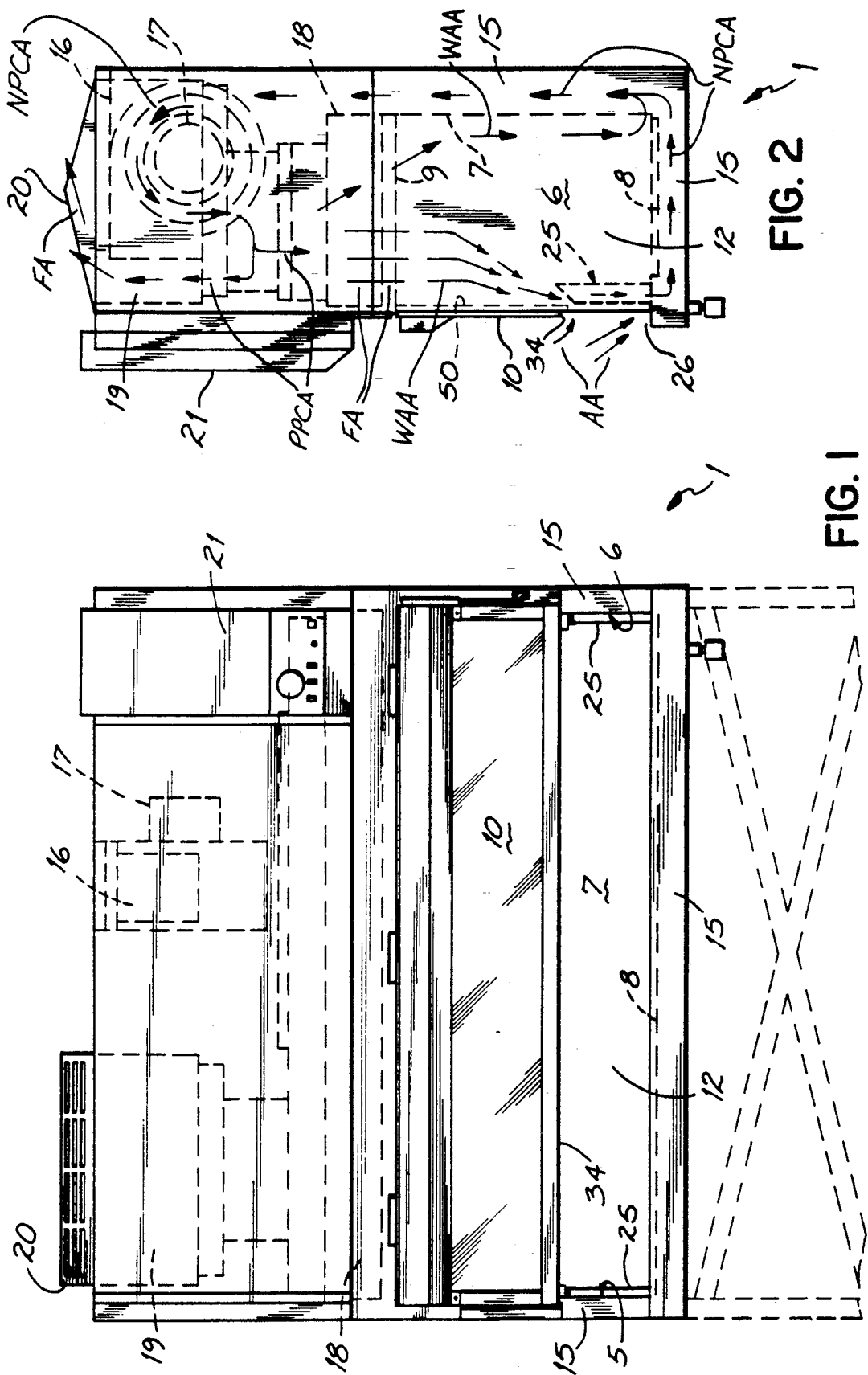

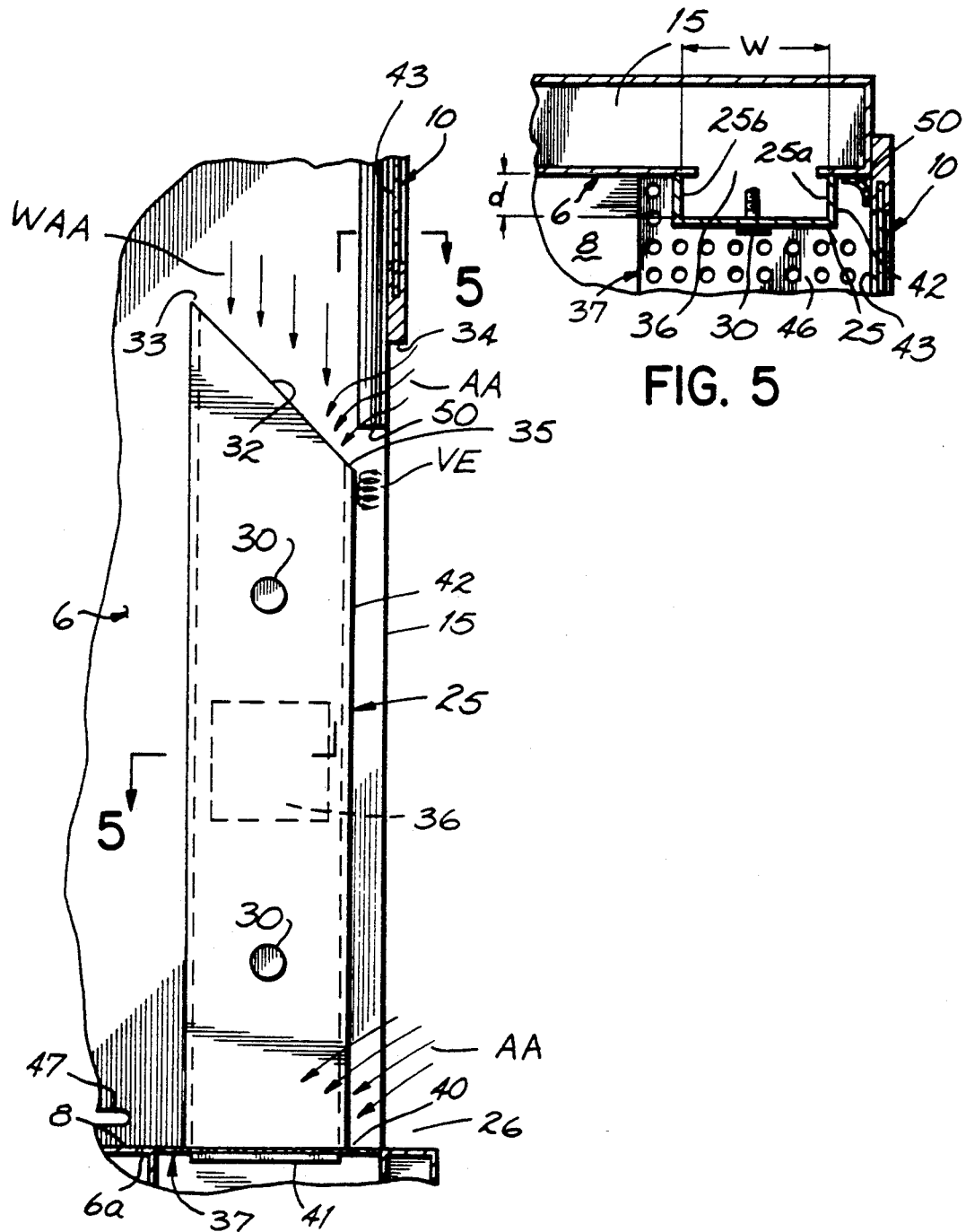

BIOLOGICAL SAFETY CABINET

FIELD OF THE INVENTION

This invention relates generally to biological safety cabinets, and more particularly to a biological safety cabinet having an improved air flow scheme which reduces the interchange of ambient air external to the cabinet with work area air internal to the cabinet.

BACKGROUND OF THE INVENTION

Biological safety cabinets currently in use have a bottom defining a work surface, a top, three sides, and a transparent front window partially covering the front of the cabinet. The cabinets are used as workbenches for biological cell culturing. Within the cabinet contaminate air is circulated through a filter downwardly through the work area onto the work surface, which work area air, after becoming contaminated, is pulled through a plenum, which surrounds a portion of the cabinet, by a blower and forced downwardly back through the filter again. A high efficiency particulate air ("HEPA") filter is generally employed to filter the air.

The window which covers a portion of the front of the cabinet is transparent to allow for viewing the contents of the work area. There is a 10 inch opening between the lower edge of the window and the threshold of the cabinet to allow for insertion of a user's arms and hands and equipment into the cabinet for placing media into, feeding and examining cell cultures on the work surface and other tasks.

The circulation of filtered air downwardly through the work area as work area air and back through the filter generates an "air curtain" which flows downwardly from the lower edge of the window towards the threshold of the safety cabinet. The threshold has an intake grill which communicates with the plenum. A negative pressure is induced within the plenum which draws the filtered air downwardly through the work area as work area air, along the inside surface of the window and downwardly towards the intake grill creating this "air curtain" effect.

A portion of the ambient air external to the cabinet also enters the intake grill at the threshold of the cabinet along the lower edge of the opening between the threshold and the window. The ambient air which enters the grill, the flow of which is generally parallel to the downwardly directed work area air curtain, is approximately the same velocity as the air curtain as the two enter the intake grill. However, near the top of the opening between the threshold and the window, the ambient air has a velocity much less than the air curtain. The work area air curtain must flow over this plane of ambient air having little velocity, and, due to friction, the velocity of the work area air curtain is reduced. Such a reduction in the velocity of the work area air curtain tends to reduce the effectiveness of the air curtain in preventing an interchange of ambient air with work area air. This phenomenon is compounded at the lateral edges of the air curtain since the velocity of the air curtain must be zero at the cabinet sidewalls, and particularly so at the upper lateral edges of the air curtain in the areas near the upper corners formed by the window and the sides of the cabinet. Therefore, when the air curtain of work area air passes the bottom edge of the window, and especially near the lateral edges of the window, the air curtain is decelerated by the ambient air and the cabinet side walls, causing the air curtain to curl outwardly out of the cabinet. Such is undesirable, as work area air is allowed to escape from the cabinet, and the strength of the air curtain is diminished thereby increasing the tendency of external disturbances, such as persons walking past the cabinet, to induce an interchange of ambient air with work area air.

It has therefore been an objective of the present invention to increase the strength of the air curtain in a biological safety cabinet.

It has been another objective of the present invention to accelerate the velocity of the ambient air external to a biological safety cabinet adjacent its air curtain in order that the difference between the velocities of the air curtain and downwardly traveling ambient air is reduced.

It has been yet another objective of the present invention to reduce the tendency of the air curtain to curl outwardly and escape from a biological safety cabinet.

SUMMARY OF THE INVENTION

In accordance with the stated objectives, the present invention is a biological safety cabinet comprising an enclosure having two side walls, a rear wall, a bottom wall defining a work surface, an air diffuser top wall and a front window, below which access can be had to the work surface, the enclosure defining a work area. The lower edge of the window is about 10 inches above the threshold of the cabinet. A plenum surrounds at least a portion of the enclosure and communicates with the work area. Means are provided for inducing a negative pressure within the plenum to circulate contaminated air through a filter within the cabinet, which creates a downwardly directed air curtain of work area air below the window. The air curtain tends to prevent the interchange of ambient air external to the enclosure with air internal to the enclosure.

A vertically oriented outwardly facing channel section is secured to each side wall adjacent the window. Each channel section has a downwardly and forwardly sloping upper end, a rear edge of which extends above the lower edge of the window and a front edge of which extends below the lower edge of the window. The plenum communicates with each channel.

Ambient air and air within the air curtain adjacent upper lateral edges of the air curtain are accelerated downwardly by the channels to reduce the tendency of the ambient air and the cabinet sidewalls to decrease a velocity of the air curtain, thereby increasing the strength of the air curtain and reducing a tendency for the ambient air and the work area air to interchange.

The upper end of the channel forms an angle of between about 40° and about 50° with respect to horizontal, and preferably is about 45°. The lower end of the channel is positioned in general juxtaposition with the cabinet threshold, and the front edge of the upper end of the channel is between about 8 inches and about 9 inches above the threshold, and the rear edge of the upper end of the channel is between about 10 inches and about 11 inches above the threshold. Preferably, the front edge is positioned about 8.569 inches above the threshold, and the rear edge is positioned about 10.509 inches above the threshold.

The channel section has an inside width dimension of between about 1.5 inches and about 2.5 inches, and preferably is about 1.922 inches. The channel has an inside depth dimension of between about 0.5 inches and about 0.6 inches, and preferably is about 0.577 inches. The channel is constructed of approximately 0.048 inches thick stainless steel sheet. A forward vertical edge of the channel is between about 0.5 inches and about 0.6 inches from an inside surface of the window, and preferably is about 0.531 inches from the inside surface of the window.

Each side wall has a hole facing the channel section which allows the plenum to communicate with the channel to induce a negative pressure at the upper end of the channel. The hole has an area of between about 2 square inches and about 2.5 square inches. Preferably, the hole is approximately centered along the height of the channel.

The threshold includes a perforated air intake grill which communicates with the plenum. The grill has a middle section with an open area of between about 35% and about 45%, and preferably is about 41% open. The grill has lateral sections each having an open area of between about 40% and about 50%, and preferably each is about 48% open. The grill preferably has along its middle section 0.094 inch holes on 9/64 inch staggered centers, and at its lateral edges 0.250 inch holes on 11/32 inch staggered centers.

One advantage of the present invention is that the tendency for work area air internal to a biological safety cabinet and ambient air external to the cabinet to interchange is reduced.

Another advantage of the present invention is that a biological safety cabinet's air curtain of work area air which tends to prevent the interchange of filtered air with ambient air is strengthened.

Yet another advantage of the present invention is that the tendency for external disturbances to induce an interchange of work area air within a biological safety cabinet with ambient air is reduced.

These and other objects and advantages of the present invention will become more readily apparent during the following detailed description taken in conjunction with the drawings herein, in which:

BRIEF DESCRIPTION OF THE DRAWINGS

FIG. 1 is a front plan view of the biological safety cabinet of the present invention;

FIG. 2 is a side plan view of the cabinet of FIG. 1;

FIG. 4 is a side plan view of the lateral side of the cabinet of FIG. 3; and

FIG. 5 is a view taken along lines 5—5 of FIG. 4.

DESCRIPTION OF PREFERRED EMBODIMENTS

Figure 3:
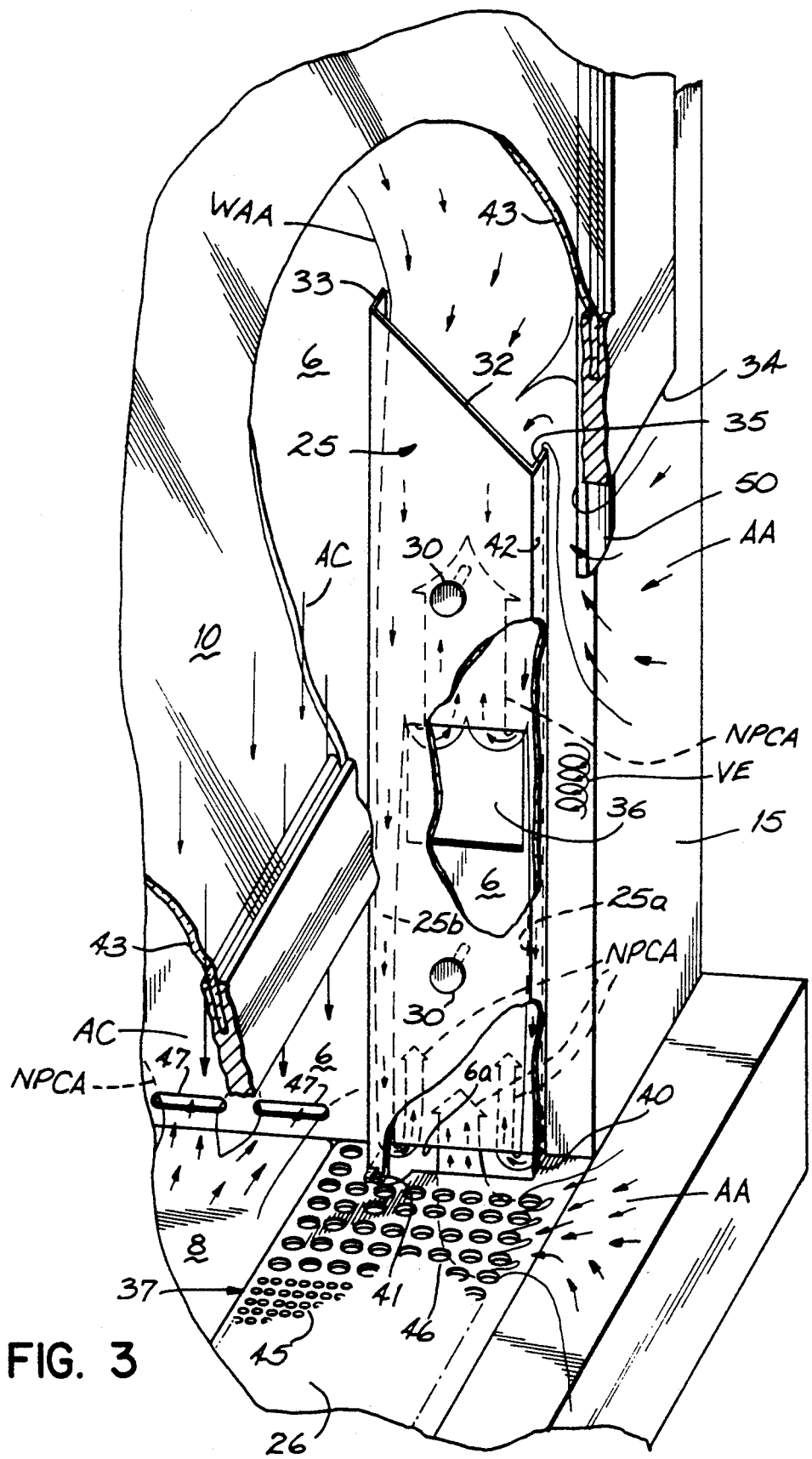
FIG. 3 is a perspective view of a lateral front side of the cabinet of FIG. 1, greatly enlarged, illustrating the channel section, grill and window and their effects on the air flow.

With reference to FIGS. 1 and 2, there is illustrated a biological safety cabinet i. The cabinet 1 includes two side walls 5 and 6, a rear wall 7, a bottom wall 8 defining a work surface, an air diffuser forming a top wall 9 and a front window 10. The side walls, rear wall, bottom and top walls and front window define an enclosure or work area 12. A plenum 15 surrounds the side walls 5 and 6, rear wall 7 and bottom wall 8 of the cabinet A blower 16 powered by a motor 17 creates a negative pressure within the plenum 15 and forces air through a high efficiency particulate air ("HEPA") filter 18 located above air diffuser or top wall 9. There is an exhaust filter at 19 and an exhaust filter guard at 20.

A control panel 21 is provided for controlling operation of the cabinet 1.

With reference to FIG. 2, the flow pattern within the safety cabinet 1 is illustrated. Negative pressure contaminated air NPCA is drawn through the plenum 15 upwardly to the blower 16. The negative pressure contaminated air NPCA continues upwardly through blower 16. Positive pressure contaminated air PPCA travels upwardly through exhaust filter 19 and downwardly through HEPA filter 18. Filtered air FA passes downwardly into the work area 12 as work area air where it becomes contaminated from the products internal to the work area 12. The work area air WAA is drawn into the plenum 15 through slots 47 in the sidewalls 5 and 6 (FIG. 3), through threshold 26 and through channel sections 25, the operation of which will be subsequently described. Ambient air AA enters the channel sections 25 as well as threshold 26 of cabinet 1 and is drawn into plenum 15.

With reference to FIG. 3, the effect of channel section 25 secured to side wall 6 of the cabinet 1 is illustrated on the air flow characteristics. It will be understood that a similar channel section 25 is secured to sidewall 5, but that only one lateral side of the cabinet is illustrated in FIG. 3 for clarity purposes. The vertically oriented channel section 2 is outwardly facing and is secured to the side wall 6 with a pair of thumb screws 30. The channel section has a downwardly and forwardly sloping upper end 32, a rear edge 33 of which extends above the lower edge 34 of the window 10, and a front edge 35 of which extends below the lower edge 34 of the window 10. In one industry standard biological safety cabinet, the lower edge 34 of the window 10 is located approximately 10 inches above the threshold 26 of the cabinet 10. A hole 36 within side wall 6 allows the plenum 15 to communicate with the channel 25 to induce a negative pressure at the upper end 32 of the channel 25.

The circulation of work area air WAA downwardly through the work area 12 and past the lower edge 34 of the window 10 creates an air curtain AC between the lower edge 34 of the window 10 and the threshold 26 of the cabinet, which has an air intake grill 37 thereon. The air intake grill 37 communicates with the plenum 15, and when a negative pressure is induced within the plenum 15 by the blower 16, the work area air curtain AC travels downwardly from the lower edge 34 of the window 10 to the intake grill 37.

A portion of the ambient air AA external to the cabinet 1 also enters through the intake grill 37 at the threshold 26. The ambient air AA entering the grill 37 is approximately the same velocity as the work area air WAA of the air curtain AC as the two enter the grill 37. However, near the top of the opening between the grill 37 and window 10 the ambient air AA has a much lower velocity than the air curtain AC. And near the lateral edges of the air curtain AC, that is along the side walls 5 and 6, the velocity of the air curtain AC must go to zero. That the work area air WAA within the air curtain AC must flow over this plane of ambient air AA having little velocity, and must flow past the sides 5 and 6 of the cabinet where its velocity goes to zero, the velocity of the work area air WAA within the air curtain AC is greatly reduced, and the reduction in the velocity tends to reduce the effectiveness of the air curtain AC in preventing an interchange of ambient air AA with work area air WAA.

The channel 25 greatly reduces this negative effect near the sides 5 and 6 of the cabinet 1. The upper end 32 of the channel 25 forms an angle of between about 40° and about 50° with respect to the horizontal, and preferably forms an angle of about 45° with respect to the horizontal. As can be seen from FIG. 2, ambient air AA enters the cabinet 1 beneath the window 10 and is immediately accelerated downwardly through the channel 25 which communicates with the plenum 15 via hole 36 in side wall 6. A portion of the downwardly directed air flow within channel 25 travels down inside forward and rearward edges 25a and 25b, respectively, of channel 25 and enters plenum 15 at the lower edge 6a of side wall 6.

More particularly, and referring to FIGS. 3-5, the channel 25 has a lower end 40 which includes an inwardly extending flange or lip 41 thereon. Grill 37 rests atop this lip 41. Therefore, lower end 40 of the channel 25 is generally in juxtaposition with the grill 37. The front edge 35 of the upper end 32 of channel 25 is between about 8 inches and about 9 inches above the threshold or grill 37. The rear edge 33 of the upper end 32 of channel 25 is between about 10 inches and about 11 inches above the grill 37. Preferably, the front edge 35 is about 8.569 inches above the grill 37, and the rear edge 33 is about 10.509 inches above the grill 37.

The channel section 25 has an inside width dimension w (FIG. 5) of between about 1.5 inches and about 2.5 inches, and preferably is about 1.922 inches. The channel 25 has an inside depth dimension d (FIG. 5) of between about 0.5 inches and about 0.6 inches, and preferably is about 0.577 inches. The channel 25 is preferably constructed of approximately 0.048 inch thick stainless steel sheet, and when constructed of such, a forward vertical edge 42 is between about 0.5 inches and about 0.6 inches from an inside surface 43 of the window 10, and preferably is about 0.531 inches from the inside surface 43 of the window 10.

Hole 36 in each side wall 5 and 6 allows plenum 15 to communicate with channel 25 to induce a negative pressure at the upper end 32 of the channel 25. The hole preferably has an area of between about 2 square inches and about 2.5 square inches, and preferably is approximately centered along the height of the channel 25.

The air intake grill 37 has a middle section 45 and two lateral sections 46. The middle section 45 has an open area of between about 35% and about 45%, and preferably is about 41% open. The lateral sections 46 are between about 40% open and about 50% open, and preferably are about 48% open. The grill preferably has, along its middle section 45, 0.094 inch holes on 9/64 inch staggered centers to create an open area of 41%. And lateral sections 46 have 0.250 inch holes on 11/32 inch staggered centers to create an open area of 48%.

With reference to FIG. 4, a wiper gasket 50 is illustrated secured to the side wall 6. The wiper gasket 50 provides a seal between window 10 and side wall 6, and is preferably fabricated of a UV resistant material, such as teflon. The wiper gasket extends downwardly below the lower edge 34 of the window 10 by approximately one inch. The wiper gasket 50 and forward vertical edge 42 of the channel 25 create an ancillary vortex effect VE as shown in FIGS. 3 and 4.

As can be appreciated from the Figures, the combination of the channel section 2 in conjunction with the grill 37 increases the strength of the air curtain AC of safety cabinet 1. The strength of the curtain is especially increased near its upper lateral edges, the points where, in traditional safety cabinets, it has been especially weak, subjecting the cabinet to a tendency of the ambient air to interchange with the filtered air.

Those skilled in the art will readily recognize numerous adaptations and modifications which can be made to the biological safety cabinet of the present invention which will result in an improved cabinet, yet all of which will fall within the spirit and scope of the present invention as defined by the appended claims and their equivalents. For example, while the invention has been disclosed for use in conjunction with one industry standard cabinet having a 10 inch high front opening, the invention has application to the other industry standard cabinet which has an 8 inch high front opening. Accordingly, the invention is intended to be limited only by the claims and their equivalents.

What is claimed is:

1. A biological safety cabinet comprising:
   an enclosure having two side walls, a rear wall, a bottom wall defining a work surface, an air diffuser top wall and a front window below which access can be had to said work surface, said enclosure defining a work area,
   a plenum surrounding at least a portion of said enclosure and communicating with said work area,
   means for inducing a negative pressure within said plenum, said means for inducing a negative pressure creating a downwardly directed air curtain of work area air below said window tending to prevent interchange of ambient air external to said enclosure with work area air internal to said enclosure, and
   a vertically oriented outwardly facing channel section secured to each side wall adjacent said window, each said channel section having a downwardly and forwardly sloping open upper end, a rear edge of which extends above a lower edge of said window and a front edge of which extends below said lower edge of said window, said plenum communicating with each said channel;
   whereby ambient air and work area air within said air curtain adjacent upper lateral edges of said air curtain are accelerated downwardly to reduce a tendency of said ambient air and said side walls to decrease a velocity of said air curtain, thereby increasing the strength of said air curtain and reducing a tendency for said ambient air and said work area air to interchange.

2. The biological safety cabinet of claim 1 wherein said upper end of said channel forms an angle of between about 40° and about 50° with respect to horizontal.

3. The biological safety cabinet of claim 2 wherein said angle is about 45°.

4. The biological safety cabinet of claim 1 wherein said lower edge of said window is about 10 inches above a threshold of said enclosure.

5. The biological safety cabinet of claim 4 wherein a lower end of said channel is generally positioned in juxtaposition with said threshold, and wherein said front edge of said upper end of said channel is between about 8 inches and about 9 inches above said threshold.

6. The biological safety cabinet of claim 5 wherein said front edge of said upper end of said channel is positioned about 8.569 inches above said threshold.

7. The biological safety cabinet of claim 4 wherein a lower end of said channel is generally positioned in juxtaposition with said threshold, and wherein said rear edge of said upper end of said channel is between about 10 inches and about 11 inches above said threshold.

8. The biological safety cabinet of claim 7 wherein said rear edge of said upper end of said channel is positioned about 10.509 inches above said threshold.

9. The biological safety cabinet of claim 1 wherein said channel has an inside width dimension of between about 1.5 inches and about 2.5 inches.

10. The biological safety cabinet of claim 9 wherein said channel has an inside width dimension of about 1.922 inches.

11. The biological safety cabinet of claim 1 wherein a forward vertical edge of said channel is between about 0.5 inches and about 0.6 inches from an inside surface of said window.

12. The biological safety cabinet of claim 11 wherein said forward vertical edge of said channel is about 0.531 inches from said inside surface of said window, and said channel is fabricated of approximately 0.048 inch thick sheet stock.

13. The biological safety cabinet of claim 1 wherein said channel has an inside depth dimension of between about 0.5 inches and about 0.6 inches.

14. The biological safety cabinet of claim 13 wherein said channel has an inside depth dimension of about 0.577 inches.

15. The biological safety cabinet of claim 1 wherein each said side wall has a hole therein facing said channel allowing said plenum to communicate with said channel to induce a negative pressure at an upper end of said channel.

16. The biological safety cabinet of claim 15 wherein said hole has an area of between about 2.0 square inches and about 2.5 square inches.

17. The biological safety cabinet of claim 16 wherein said hole is approximately centered along a height of said channel.

18. The biological safety cabinet of claim 1 wherein a threshold of said enclosure has an air intake grill thereon, said grill having a center section with an open area of between about 35% and about 45%, and lateral sections with an open area of between about 40% and about 50%.

19. The biological safety cabinet of claim 18 wherein said center section is about 41% open and said lateral sections are about 48% open.

20. The biological safety cabinet of claim 19 wherein said center section has 0.094 inch holes on 9/64 inch staggered centers, and said lateral sections have 0.250 inch holes on 11/32 inch staggered centers.

21. A biological safety cabinet comprising:
an enclosure having two side walls, a rear wall, a bottom wall defining a work surface, an air diffuser top wall and a front window below which access can be had to said work surface, said enclosure defining a work area;
a plenum surrounding at least a portion of said enclosure and communicating with said work area;
means for inducing a negative pressure within said plenum, said means for inducing a negative pressure creating a downwardly directed air curtain of work area air below said window tending to prevent interchange of ambient air external to said enclosure with work area air internal to said enclosure; and
a vertically oriented outwardly facing channel section having an open upper end secured to each said side wall adjacent said window, said plenum communicating with each said channel;
whereby ambient air and work area air within said air curtain adjacent upper lateral edges of said air curtain are accelerated downwardly to reduce a tendency of said ambient air and said side walls to decrease a velocity of said air curtain, thereby increasing the strength of said air curtain and reducing a tendency for said ambient air and said work area air to interchange.

22. The biological safety cabinet of claim 21 wherein each said channel section upper end is downwardly and forwardly sloping.

23. A biological safety cabinet comprising:
an enclosure having two side walls, a rear wall, a bottom wall defining a work surface and a front window below which access can be had to said work surface, said enclosure defining a work area,
a plenum surrounding at least a portion of said enclosure and communicating with said work area,
means for inducing a negative pressure within said plenum, said means for inducing a negative pressure creating a downwardly directed air curtain of work area air below said window tending to prevent interchange of ambient air external to said enclosure with work area air internal to said enclosure, and
a vertically oriented outwardly facing channel section secured to each side wall adjacent said window, each said channel section having a downwardly and forwardly sloping open upper end, a rear edge of which extends above a lower edge of said window and a front edge of which extends below said lower edge of said window, said plenum communicating with each said channel;
whereby ambient air and work area air within said air curtain adjacent upper lateral edges of said air curtain are accelerated downwardly to reduce a tendency of said ambient air and said side walls to decrease a velocity of said air curtain, thereby increasing the strength of said air curtain and reducing a tendency for said ambient air and said work area air to interchange.

24. A biological safety cabinet comprising:
an enclosure having two side walls, a rear wall, a bottom wall defining a work surface and a front window below which access can be had to said work surface, said enclosure defining a work area;
a plenum surrounding at least a portion of said enclosure and communicating with said work area;
means for inducing a negative pressure within said plenum, said means for inducing a negative pressure creating a downwardly directed air curtain of work area air below said window tending to prevent interchange of ambient air external to said enclosure with work area air internal to said enclosure; and
a vertically oriented outwardly facing channel section having an open upper end secured to each said side wall adjacent said window, said plenum communicating with each said channel;
whereby ambient air and work area air within said air curtain adjacent upper lateral edges of said air curtain are accelerated downwardly to reduce a tendency of said ambient air and said side walls to decrease a velocity of said air curtain, thereby increasing the strength of said air curtain and reducing a tendency for said ambient air and said work area air to interchange.

* * * * *

UNITED STATES PATENT AND TRADEMARK OFFICE
CERTIFICATE OF CORRECTION

PATENT NO. :   5,295,902
DATED       :   March 22, 1994
INVENTOR(S) :   Kuah T. Hock It is certified that error appears in the above-identified patent and that said Letters Patent is hereby corrected as shown below:

Column 3, line 57, "cabinet i" should be -- cabinet 1 --.

Column 3, line 63, "cabinet" should be -- cabinet 1 --.

Column 4, line 26, "section 2" should be -- section 25 --.

Column 5, line 65, "section 2" should be -- section 25 --.

Column 7, line 21, "claim i" should be -- claim 1 --.

Signed and Sealed this

Eighth Day of November, 1994

Attest:

BRUCE LEHMAN

Attesting Officer

Commissioner of Patents and Trademarks